(12) United States Patent
Marino

(10) Patent No.: US 6,739,112 B1
(45) Date of Patent: May 25, 2004

(54) BONE ALLOGRAFT PACKAGING SYSTEM

(75) Inventor: James F. Marino, La Jolla, CA (US)

(73) Assignee: Nu Vasive, Inc., San Diego, CA (US)

( * ) Notice: Subject to any disclaimer, the term of this patent is extended or adjusted under 35 U.S.C. 154(b) by 0 days.

(21) Appl. No.: 09/687,611

(22) Filed: Oct. 11, 2000

Related U.S. Application Data
(60) Provisional application No. 60/226,660, filed on Aug. 21, 2000.

(51) Int. Cl.[7] .............................................. B65B 55/22
(52) U.S. Cl. ............................. 53/431; 53/432; 53/440; 128/898; 260/438; 623/23.63
(58) Field of Search .................. 53/428, 431, 432–434, 53/440, 441, 480, 485; 128/898; 206/438; 623/23.63

(56) References Cited

U.S. PATENT DOCUMENTS

| | | | |
|---|---|---|---|
| 4,065,816 A | * | 1/1978 | Sawyer ..................... 53/431 X |
| 5,480,424 A | * | 1/1996 | Cox ........................... 623/2.15 |
| 5,531,791 A | * | 7/1996 | Wolfinbarger, Jr. ...... 623/23.63 |
| 5,989,498 A | * | 11/1999 | Odland ................... 623/918 X |
| 6,294,187 B1 | * | 9/2001 | Boyce et al. ............... 424/422 |

* cited by examiner

*Primary Examiner*—Stephen F. Gerrity
(74) *Attorney, Agent, or Firm*—Jonathan Spangler

(57) ABSTRACT

A system for packaging a bone allograft for use in a future medical procedure in which the bone allograft is stored in a saturated saline solution in an airtight container. The saline solution keeps the allograft hydrated and may be saturated with a combination of calcium, phosphate, or magnesium to inhibit mineral leaching out of the allograft during storage. The container may be deformable to conform to the shape of the allograft material as the container is "shrink-fitted" to the allograft. Optionally, the bone allograft may also be freeze dried prior to placement in the container.

31 Claims, 5 Drawing Sheets

BONE ALLOGRAFT PACKAGING SYSTEM

CROSS-REFERENCES TO RELATED APPLICATIONS

This application is a continuation of, and claims the benefit of priority from provisional application No. 60/226,660, filed on Aug. 21, 2000, the full disclosure of which is incorporated herein by reference.

TECHNICAL FIELD

The present invention relates to allograft packaging systems, and more particularly to bone allograft packaging systems.

BACKGROUND OF THE INVENTION

Bone allografts are used in a variety of medical procedures, e.g., spinal fusion procedures. Such bone allografts need first to be processed at a sanctioned facility and then are provided to medical facilities that perform the procedures. These processing facilities may shape bone allografts and then package them for transportation to medical facilities. Commonly, the bone allografts are either: (1) fresh frozen or (2) freeze dried prior to packaging and transportation to a medical facility. Disadvantages exist with both of these approaches. Specifically, fresh frozen bone allografts must be continuously stored at low temperatures (ie: frozen) both when stored and when transported to the medical facility to ensure their suitability for future medical procedures. Disadvantages of requiring such refrigerated storage include both the cost incurred in operating such equipment and the preparation time required in thawing the allografts for use at the start of the medical procedure. On the other hand, when using freeze dried bone allografts, the bone allografts must be re-hydrated prior to use in a medical procedure (which may require some time). Moreover, during the re-hydration process, the bone allograft must be kept in a sterile environment. Due to the time required either to thaw fresh frozen bone allografts or to re-hydrate freeze dried bone allografts, the thawing/re-hydration of the allografts must be commenced a period of time prior to actually starting the medical procedure, thus increasing the overall time required to perform the surgical procedure.

A further disadvantage of using a freeze dried bone allograft is that the freeze-drying process reportedly reduces the mechanical properties of the bone (for example, its compressive strength and rigidity). Rehydrating the bone is reported to restore only about 90% of the original properties, and this restoration is dependent on physician compliance with the rehydration process.

Moreover, in certain medical procedures the size or shape of the bone allograft required may not be known a priori. Consequently, several different size/shape bone allografts may need to be thawed/re-hydrated prior to the medical procedure. Those allografts not used during the procedure then need to be discarded. This is an inefficient use of a limited resource (bone allograft) and is time consuming. Accordingly, a need exists for an improved system for packaging bone allografts for future medical procedures, and in particular a system in which the allografts can be readied for surgical use much more quickly than with existing methods.

The present invention includes systems for packaging and storing bone allograft material for future use in a medical procedure. In accordance with the present invention, the bone allograft may be placed in a container. In various aspects of the invention, this container may comprise glass, plastic, or a metal foil. A saline solution may be added to the container. In one aspect of the invention, the amount of saline solution added is preferably just sufficient to keep the bone allograft hydrated. In one preferred aspect of the invention, the saline solution is saturated with minerals to minimize the leaching of minerals from the bone over time. The saturation of the saline solution may be accomplished with any combination of minerals, including, but not limited to, calcium, phosphate and magnesium.

After placing the bone allograft in a saline solution in the container, the container may then optionally be closed with an airtight seal. Prior to the medical procedure, the bone allograft is then simply removed from the container for use. In one optional aspect of the invention, the bone allograft may be sealed in a container with solution then added to the container via a self-sealing valve. In one approach, air may be vacuumed from the container prior to closing the container. When using this approach, a "shrink-wrap" type of container may be used in which the container conforms to the shape of the allograft as the air is vacuumed out.

Although not required by the present invention, the bone allograft may optionally be freeze-dried as well prior to insertion in the container where it is then re-hydrated and kept hydrated. An advantage of such optional freeze-drying is that it may reduce the antigenicity of the bone allograft.

Advantages of the present system of bone allograft storage packaging include the elimination of refrigeration requirements, thereby providing allografts which can be quickly prepared for use by a physician when performing a medical procedure. This reduces the overall cost of system operation as refrigeration equipment is not required, either when storing or transporting the allograft material. A second advantage is that considerable time is not wasted in thawing or re-hydrating the allograft material before transplanting it into a patient.

Preferably as well, the packaging material and the saline solution are sterilized such that the bone allograft can be removed ready for use in a sterilized condition.

BRIEF DESCRIPTION OF THE DRAWINGS

Like reference numbers and designations in the various drawings indicate like elements.

DESCRIPTION OF THE SPECIFIC EMBODIMENTS

Throughout this description, the preferred embodiment and examples shown should be considered as exemplars, rather than as limitations on the present invention.

Figure 1:
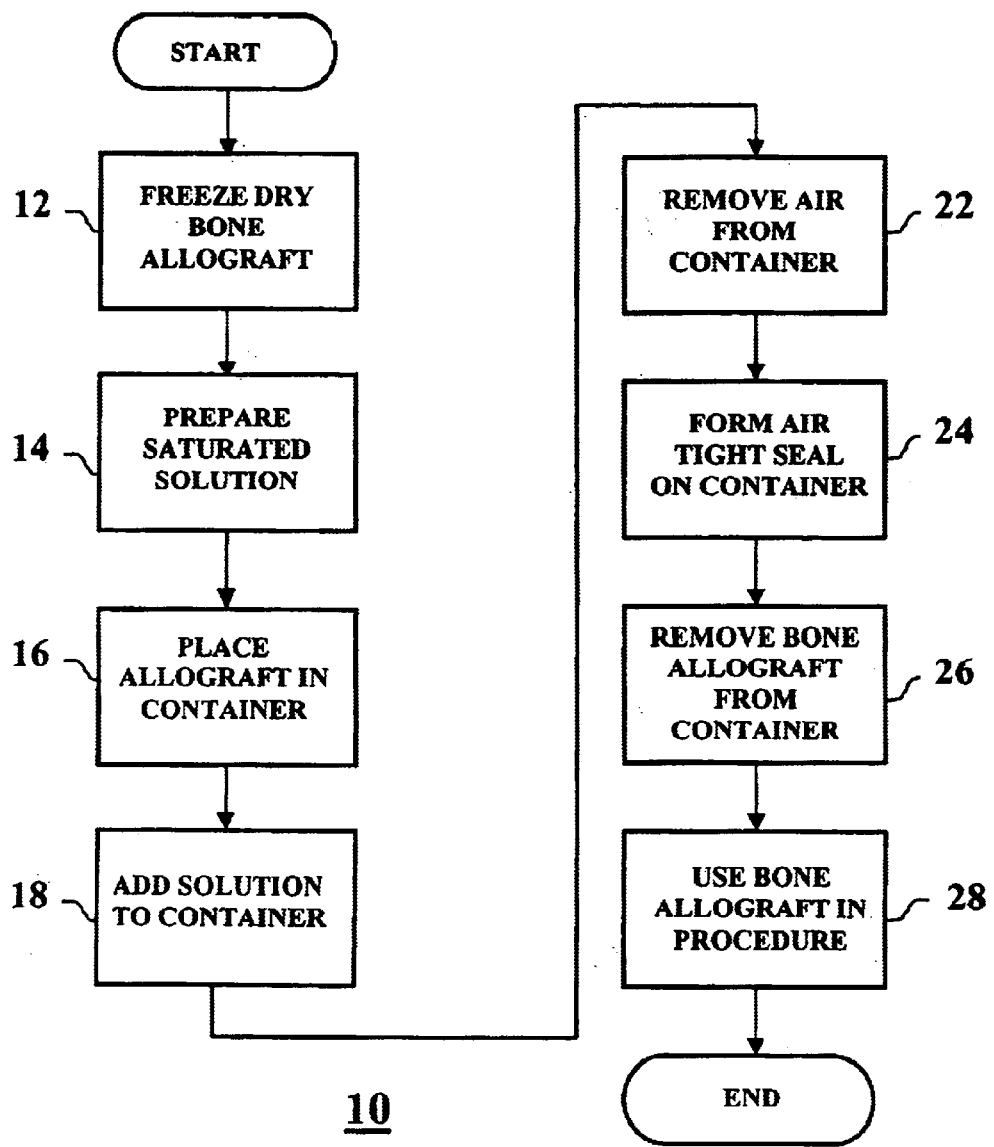
FIG. 1 is a flowchart of a method of packaging a bone allograft for storage to be used in a future medical procedure in accordance with the present invention.

FIG. 1 is a flowchart of one method 10 of packaging and storing a bone allograft for use in a future medical procedure. In accordance with the present invention, the bone allograft is placed in an airtight container in a saturated saline solution, such that the bone allograft may be removed for use just prior to the medical procedure. In one optional aspect, method 10 includes freeze drying the bone allograft (step 12). Advantageously, freeze drying the bone allograft may reduce antigenicity of the bone allograft. In other preferred aspects of the present invention, however, this freeze drying step (12) is bypassed. A saturated solution is prepared (step 14) to be added into the container (step 18). The addition of saline solution to the container may be carried out after, before or concurrently with the placement of the bone allograft in the container (step 16). A simple (ie: non-saturated) saline solution may also be used so that step 14 (the preparation of a saturated saline solution) may also be bypassed in some aspects of the invention.

Figure 2:
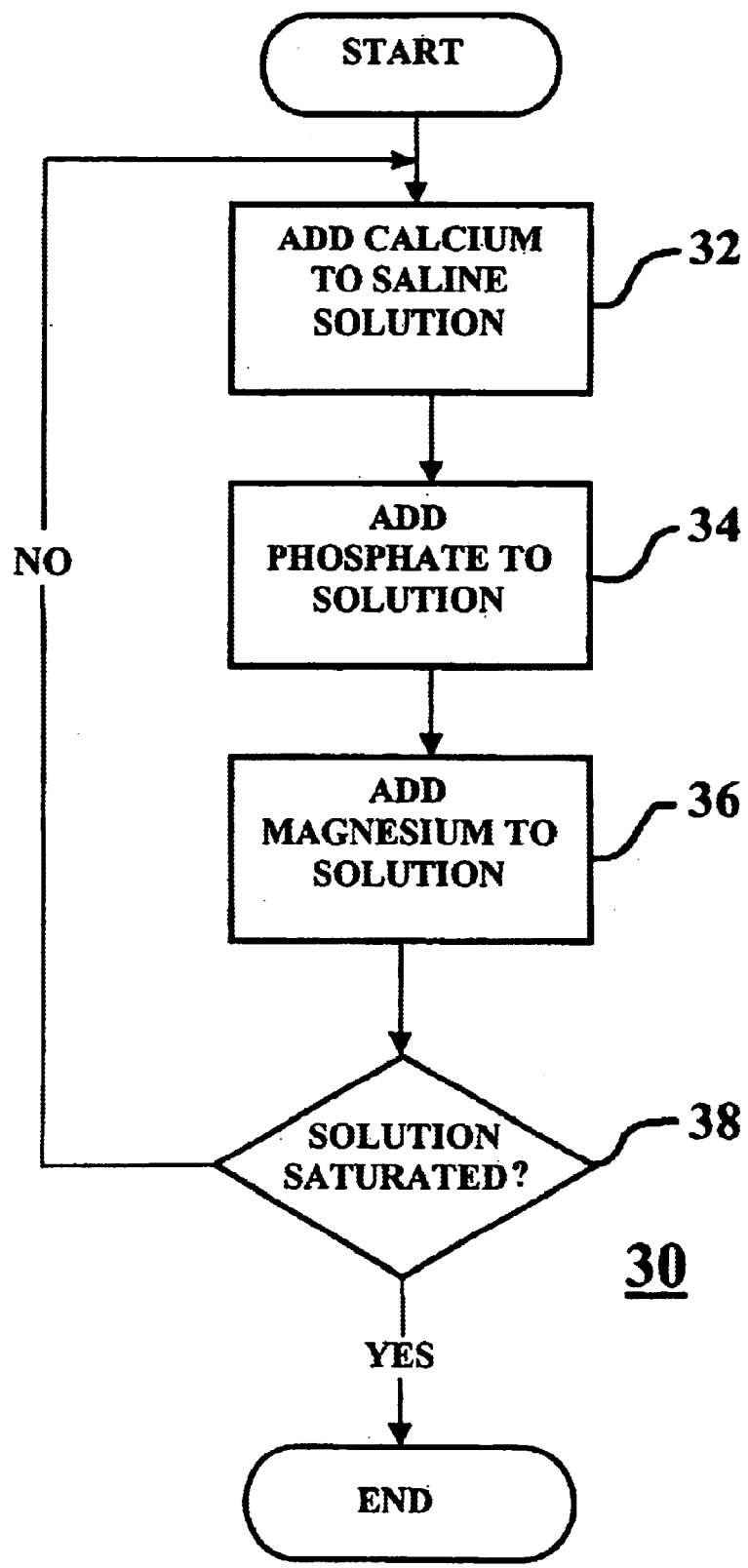
FIG. 2 is a flowchart of a method of preparing a saturated saline solution for use in the method shown in FIG. 1.

One exemplary method 30 of preparing the saturated solution (step 14) is shown in FIG. 2. (The present invention is not limited to this particular method of preparing a saline solution. Rather, any suitable method of preparing the saline solution is also within the scope of the present invention).

As shown in FIG. 2, calcium may optionally be added to the solution (step 32), phosphate may optionally be added to the solution (step 34), and magnesium may optionally be added to the solution (step 36) until the solution is saturated (step 38). In accordance with the present invention, none, some or all of steps 32, 34, 36 may be carried out when preparing the saline solution. In addition, the saline solution may optionally be buffered (to have a neutral pH). The solution so prepared (which may comprise a calcium, phosphate, magnesium salt saturated saline solution) is then added to the bone allograft in the container (step 18). In various optional aspects, other minerals or elements may also be added to the solution, advantageously decreasing mineral leaching from the bone allograft during storage in the container.

Optionally, the amount of solution added to the container is just sufficient to keep the bone allograft hydrated. The solution may optionally be a saline solution or a saturated saline solution. In various optional aspects of the invention in which the bone allograft is freeze dried (step 12) prior to being placed in the container, the amount of solution added is preferably just sufficient to re-hydrate the bone allograft and keep the bone allograft hydrated.

In various aspects of the present invention, the container 40 (FIG. 3) in which allograft 42 is stored may be made from glass, plastic, metal foil, or a combination of these or different materials. Container 40 may optionally be sealed with an airtight seal (step 24 in FIG. 1), for example by a lid 44 placed over container 40 (preferably after air is evacuated (step 22) from container 40). After the air has been evacuated from container 40, bone allograft 42 may then be packaged and stored in a saturated solution 46 (prepared as described above) in container 40, which is preferably airtight. Immediately before allograft 42 is required for use, lid 44 is removed from container 40 and allograft material 42 is removed, already being in a hydrated state.

Figure 3:
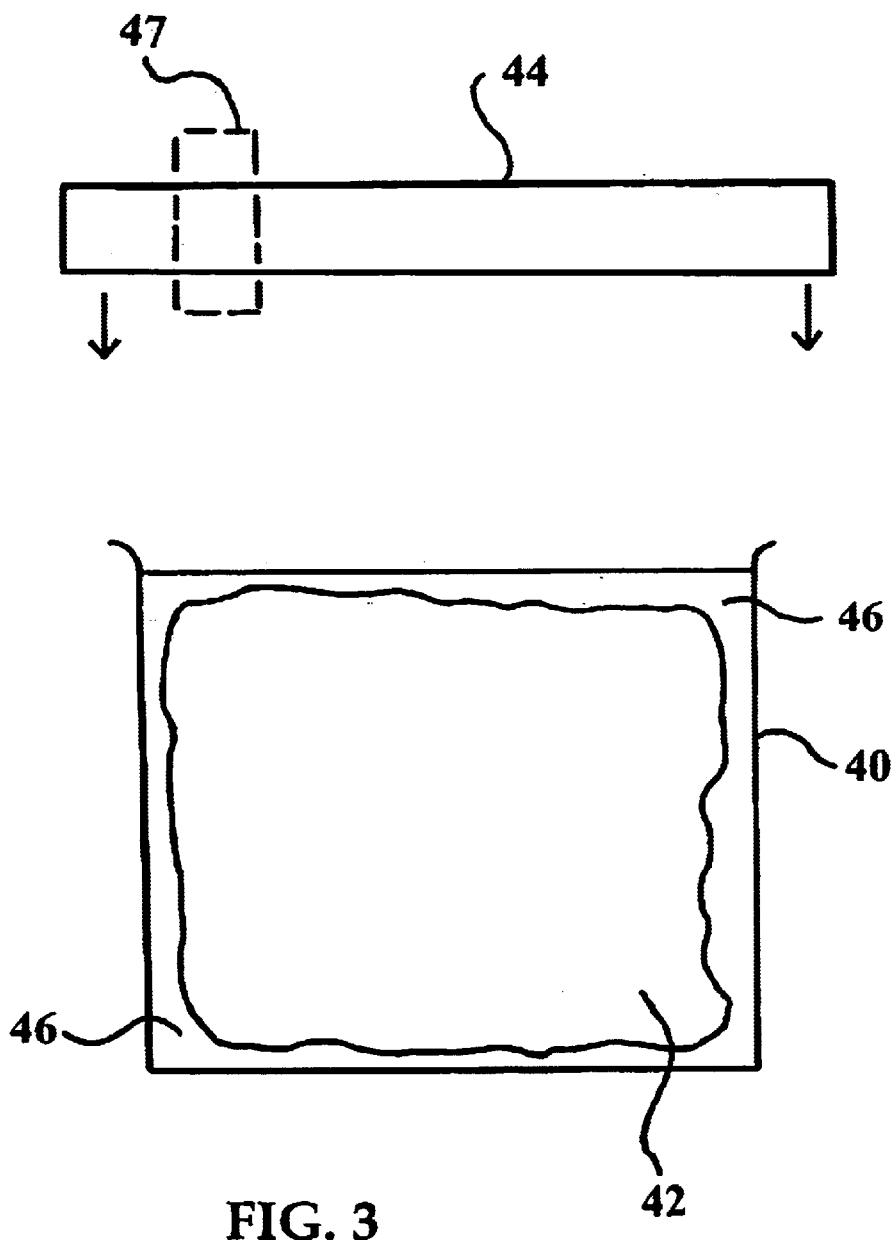
FIG. 3 is an illustration of bone allograft material stored in a saline solution in a container in accordance with the present invention.

For illustration purposes, allograft 42 is shown submersion in solution 46 in FIGS. 3 and 5. It is to be understood that although allograft 42 is submersed in solution 46 in some cases, the present system requires only enough of solution 46 be used to keep allograft 42 hydrated.

Advantageously, due to the saturation of the solution, the amount of materials leaching from bone allograft 42 into solution 46 will be minimal. In addition, the presence of calcium, phosphate, and magnesium salts in solution 46 may encourage re-mineralization of the bone allograft during storage in container 40. Consequently, bone allograft 42 may conceivably be stored for an indefinite period of time prior to use in a medical procedure.

A further advantage of the present packaging/storage system is that the bone allograft need not be kept in a low temperature environment either during storage in the packaging or during transportation to a medical facility. As such, the bone allograft may advantageously be kept at room temperature during both storage and transportation. As explained above, prior to use in a medical procedure, the bone allograft is simply removed (step 26 in FIG. 1) from the sealed container for use in the medical procedure (step 28 in FIG. 1).

Figure 4A:
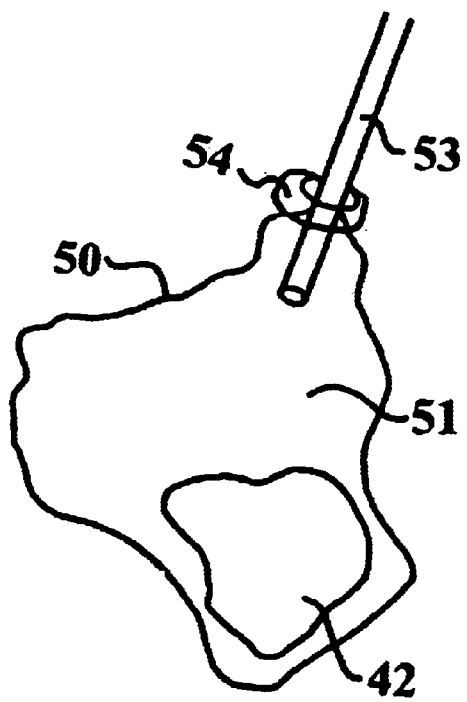
FIGS. 4A and 4B are illustrations of bone allograft material stored in a saline solution in a shape conformable "shrink-wrap" type container in accordance with the present invention.
Figure 4B:
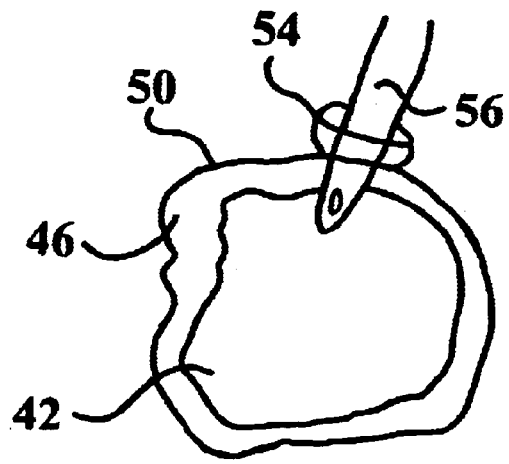

In another optional preferred aspect of the invention shown in FIGS. 4A and 4B, bone allograft 42 is sealed and packaged in a "shrink-wrap" type of shape-conforming material 50. Conforming material 50 may include foil and plastic. In one approach, bone allograft 42 is placed into conforming material 50, air 51 is removed by tube 53, causing conforming material 50 to become "shrink wrapped" around bone allograft 42 as shown in FIG. 4B. Thereafter, solution 46 is added into the shrink wrapped package of conforming material 50, for example by needle 56 inserted through self-sealing valve 54, thereby keeping allograft material 42 hydrated and readied for immediate or near-immediate use. In this aspect of the invention, the amount of solution added to the packaging is preferably just sufficient to keep the bone allograft hydrated.

Figure 5A:
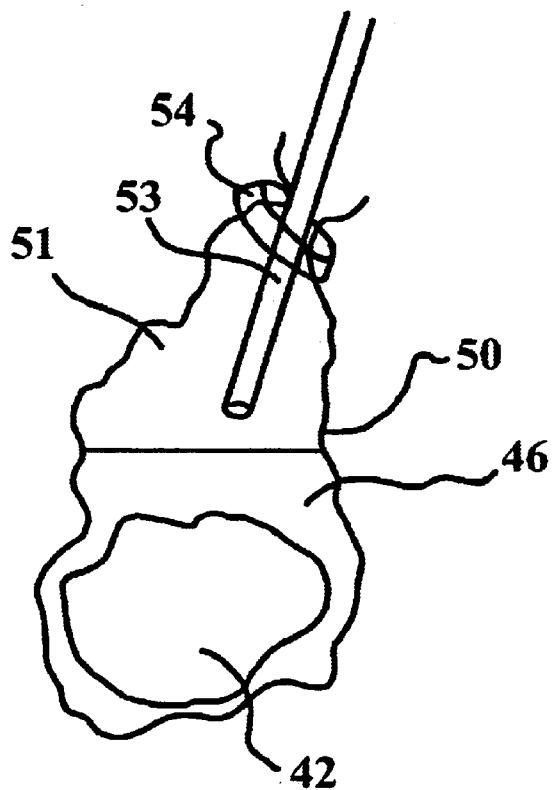
FIGS. 5A and 5B are illustrations of bone allograft material stored in a saline solution in a shape conformable "shrink-wrap" type container in accordance with another method of the present invention.
Figure 5B:
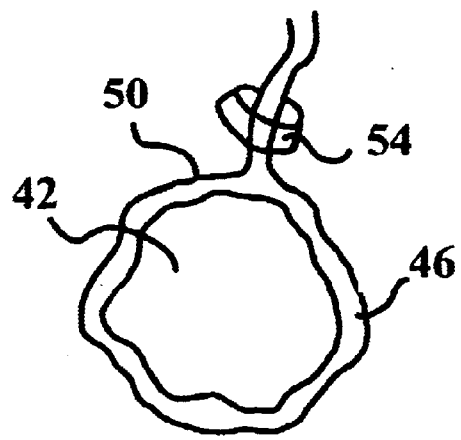

Alternatively, as shown in FIGS. 5A and 5B, bone allograft 42 and solution 46 can be first added together into conforming material 50, which is then shrink fitted over hydrated allograft 42 by removing air 51 and a portion of solution 46. Specifically, as shown in FIG. 5A, bone allograft 42 is placed into conforming material 50. Thereafter, air 51 is vacuum removed from conforming material 50 such that it wraps tightly around bone allograft 42 as shown in FIG. 5B. In this aspect of the invention, a portion of solution 46 may also be removed from conforming material 50 as air 51 is removed. However, sufficient solution 46 remains within conforming material 50 (and specifically within bone allograft 42) such that bone allograft 42 remains hydrated, and ready for immediate or near-immediate use. As shown in FIG. 5A, a suction tube 53 may be used to remove air 51 (and a portion of solution 46). As shown in FIG. 5B, a clamp (or a self-sealing valve) 54 may be used to prevent air from entering the package provided by conforming material 50.

In another optional aspect of the invention, solution 46 may be inserted in container 40 (FIG. 3) by first inserting a hollow needle (not shown) through an optional self sealing valve 47 passing through lid 44 and then injecting the solution through the needle.

While this invention has been described in terms of a best mode for achieving this invention's objectives, it will be appreciated by those skilled in the art that variations may be accomplished in view of these teachings without deviating from the spirit or scope of the present invention.

What is claimed is:

1. A method of providing a bone allograft for use in spinal fusion surgery, comprising:

processing an article of human bone to form a bone allograft dimensioned for use in spinal fusion surgery; and sealing said bone allograft in a container having a volume of saline solution disposed therein, said volume of saline solution being provided in an amount sufficient to maintain said bone allograft in a substantially submerged state while in said container such that, until use, said bone allograft will be maintained in a hydrated state and thereby avoid the need to rehydrate said bone allograft prior to use in spinal fusion surgery.

2. The method of providing a bone allograft for use in spinal fusion surgery of claim 1, wherein said saline solution is a saturated saline solution.

3. The method of providing a bone allograft for use in spinal fusion surgery of claim 1, wherein said volume of saline solution in said container is just sufficient to hydrate said bone allograft.

4. The method of providing a bone allograft for use in spinal fusion surgery of claim 1, wherein said container is self conforming to the shape of said bone allograft.

5. The method of providing a bone allograft for use in spinal fusion surgery of claim 1, wherein said container comprises a self-sealing valve and wherein said saline solution is added to said container via said self-sealing valve after said container is sealed.

6. The method of providing a bone allograft for use in spinal fusion surgery of claim 1, wherein sealing said container comprises:
  removing air from said container; and
  sealing said container.

7. The method of providing a bone allograft for use in spinal fusion surgery of claim 1, wherein said saline solution is added to the container by:
  preparing a saturated saline solution; and
  introducing said saturated saline solution into said container.

8. The method of providing a bone allograft for use in spinal fusion surgery of claim 7, wherein preparing said saturated saline solution comprises adding at least one of calcium and phosphate to a saline solution until said saline solution is saturated.

9. The method of providing a bone allograft for use in spinal fusion surgery of claim 7, wherein preparing said saturated saline solution comprises adding at least one of calcium, phosphate, and magnesium to a saline solution until said saline solution is saturated.

10. The method of providing a bone allograft for use in spinal fusion surgery of claim 1, wherein placing said bone allograft in said container comprises:
  freeze drying said bone allograft prior to introduction into said container; and
  placing said bone allograft in said container.

11. The method of providing a bone allograft for use in spinal fusion surgery of claim 10, wherein placing said bone allograft in a container comprises adding a saline solution to said container until said bone allograft is re-hydrated.

12. The method of providing a bone allograft for use in spinal fusion surgery of claim 1, wherein said container consists primarily of one of glass, plastic, and metal foil.

13. A method of using a bone allograft in a spinal fusion procedure, comprising:
  opening, prior to use in a spinal fusion procedure, a container having a bone allograft disposed therein, said bone allograft dimensioned for use in a spinal fusion procedure and substantially submerged in a volume of saline solution disposed within said container such that, during transportation and storage, said bone allograft will be maintained in a substantially hydrated state.

14. The method of using a bone allograft in a spinal fusion procedure of claim 13, wherein said saline solution disposed within said container comprises a saturated saline solution.

15. The method of using a bone allograft in a spinal fusion procedure of claim 13, wherein said volume of saline solution disposed within said container is just sufficient to hydrate said bone allograft.

16. The method of using a bone allograft in a spinal fusion procedure of claim 13, wherein said container self conforms to the shape of said bone allograft.

17. The method of using a bone allograft in a spinal fusion procedure of claim 13, wherein said container comprises a self-sealing valve and wherein said saline solution is introduced into said container via said self-sealing valve after said container is sealed.

18. The method of using a bone allograft in a spinal fusion procedure of claim 13, wherein said container is sealed after first removing air from said container.

19. The method of using a bone allograft in a spinal fusion procedure of claim 13, wherein said saline solution is added to said container by:
  preparing a saturated saline solution; and
  introducing said saturated saline solution to said container.

20. The method of using a bone allograft in a spinal fusion procedure of claim 19, wherein preparing said saturated saline solution comprises adding at least one of calcium and phosphate to a saline solution until said saline solution is saturated.

21. The method of using a bone allograft in a spinal fusion procedure of claim 19, wherein preparing said saturated saline solution comprises adding at least one of calcium, phosphate, and magnesium to a saline solution until said saline solution is saturated.

22. The method of using a bone allograft in a spinal fusion procedure of claim 13, wherein said bone allograft is placed into said container after said bone allograft is freeze dried.

23. The method of using a bone allograft in a spinal fusion procedure of claim 22, wherein said bone allograft is re-hydrated by the introduction of said saline solution into said container.

24. The method of using a bone allograft in a spinal fusion procedure of claim 13, wherein said container consists primarily of one of glass, plastic, and metal foil.

25. A system for storing a bone allograft prior to use in spinal fusion surgery, comprising:
  a container having a volume of saline solution disposed therein; and
  a bone allograft sealed within the container, said bone allograft being dimensioned for use in spinal fusion surgery and substantially submerged in said saline solution while sealed in said container such that, until use, said bone allograft will be maintained in a hydrated state.

26. The system for storing a bone allograft prior to use in spinal fusion surgery of claim 25, wherein said saline solution comprises at least one of the minerals selected from the group consisting of calcium, phosphate and magnesium.

27. The system for storing a bone allograft prior to use in spinal fusion surgery of claim 25, wherein said container includes an airtight seal.

28. The system for storing a bone allograft prior to use in spinal fusion surgery of claim 25, wherein the shape of said container is deformable to the shape of said bone allograft.

29. The system for storing a bone allograft prior to use in spinal fusion surgery of claim 25, wherein said container has a self-sealing valve, further comprising:
  a needle for injecting said saline solution through said self sealing valve and into said container.

30. A method of performing a spinal fusion procedure, comprising:
  opening a container having a bone allograft disposed therein, said bone allograft dimensioned for use in a spinal fusion procedure and substantially submerged in a volume of saline solution disposed within said container such that, during transportation and storage, said bone allograft will be maintained in a substantially hydrated state;
  removing said bone allograft from said container; and disposing said bone allograft between adjacent vertebral bodies within the human spine such that, over time, said vertebral bodies will fuse together.

31. A method of avoiding the need to re-hydrate bone allograft immediately prior to performing a spinal fusion procedure, comprising:

providing within a sealed container a bone allograft dimensioned for use in a spinal fusion procedure; and providing a volume of saline solution within said sealed container in an amount sufficient to maintain said bone allograft in a substantially submerged state such that said bone allograft will be maintained in a hydrated state until use.

\* \* \* \* \*